(12) United States Patent
Karp et al.

(10) Patent No.: US 6,845,787 B2
(45) Date of Patent: Jan. 25, 2005

(54) MICROFLUIDIC MULTI-SPLITTER

(75) Inventors: Christoph D. Karp, Pasadena, CA (US); Adrian Hightower, Pasadena, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/371,812

(22) Filed: Feb. 21, 2003

(65) Prior Publication Data

US 2003/0159742 A1 Aug. 28, 2003

Related U.S. Application Data

(60) Provisional application No. 60/359,323, filed on Feb. 23, 2002.

(51) Int. Cl.[7] .................................................. F15C 1/06
(52) U.S. Cl. ....................... 137/833; 422/100; 422/101; 204/601
(58) Field of Search .......................... 137/833; 422/100, 422/101; 204/601

(56) References Cited

U.S. PATENT DOCUMENTS

| | | | | |
|---|---|---|---|---|
| 3,495,608 A | * | 2/1970 | O'Keefe | 137/815 |
| 3,548,849 A | * | 12/1970 | Jahnke et al. | 137/815 |
| 3,568,692 A | * | 3/1971 | Metzger et al. | 137/81.5 |
| 3,587,615 A | | 6/1971 | Thomson | 137/81.5 |
| 5,637,469 A | * | 6/1997 | Wilding et al. | 435/7.21 |
| 5,846,396 A | | 12/1998 | Zanzucchi et al. | 204/601 |
| 5,955,029 A | | 9/1999 | Wilding et al. | 422/68.1 |
| 6,074,725 A | * | 6/2000 | Kennedy | 428/188 |
| 6,090,251 A | | 7/2000 | Sundberg et al. | 204/453 |
| 6,103,199 A | | 8/2000 | Bjornson et al. | 422/100 |
| 6,136,272 A | * | 10/2000 | Weigl et al. | 422/82.05 |
| 6,154,226 A | | 11/2000 | York et al. | 346/140.1 |
| 6,193,471 B1 | | 2/2001 | Paul | 417/53 |
| 6,296,020 B1 | * | 10/2001 | McNeely | 137/806 |
| 6,494,230 B2 | | 12/2002 | Chow | 137/827 |
| 6,494,614 B1 | | 12/2002 | Bennett et al. | 366/336 |
| 6,499,499 B2 | * | 12/2002 | Dantsker et al. | 137/1 |
| 6,532,978 B1 | | 3/2003 | Muller-Kuhrt et al. | 137/1 |
| 6,537,506 B1 | | 3/2003 | Schwalbe et al. | 422/130 |
| 6,623,860 B2 | * | 9/2003 | Hu et al. | 428/411.1 |
| 6,645,432 B1 | * | 11/2003 | Anderson et al. | 422/100 |
| 6,648,015 B1 | * | 11/2003 | Chow | 137/557 |

FOREIGN PATENT DOCUMENTS

| | | | | |
|---|---|---|---|---|
| EP | 1 106 244 A2 | | 6/2001 | |
| WO | WO 97/00125 | * | 1/1997 | B01F/5/06 |
| WO | WO 98/54568 | * | 12/1998 | G01N/30/60 |
| WO | WO 99/19717 | * | 4/1999 | G01N/25/22 |
| WO | WO 99/48599 | | 9/1999 | |
| WO | WO 99/60397 | * | 11/1999 | G01N/33/483 |
| WO | WO 99/61888 | * | 12/1999 | G01N/15/14 |
| WO | WO 00/21659 | | 4/2000 | |
| WO | WO 00/22436 | * | 4/2000 | G01N/33/567 |
| WO | WO 01/04909 A1 | | 1/2001 | |
| WO | WO 01/74490 A2 | | 10/2001 | |

OTHER PUBLICATIONS

McNeely, M.R., et al., "Hydrophobic Microfluidics," SPIE Microfluidic Devices and Systems II, vol. 3877, Santa Clara, CA, Sep. 1999, pp. 210–220.*

Puntambekar, Aniruddha, et al., "An Air–Driven Fluidic Multiplexer Integrated with Microdispensers," *Micro Total Analysis Systems 2001*, J.M. Ramsey and A. van den Berg (eds.), Kluwer Academic Publishers, Netherlands, 2001, pp. 78–80.

* cited by examiner

*Primary Examiner*—A. Michael Chambers
(74) *Attorney, Agent, or Firm*—Vincent K. Gustafson; Michael F. Labbee (57) ABSTRACT

A splitter for multi-layer microfluidic devices is provided. The splitter includes multiple forked channels defined in two or more device layers. The forked channels communicate fluidically at overlap regions. The overlap regions, in combination with symmetrical channel geometries balance the fluidic impedance in the system and promote even splitting.

24 Claims, 13 Drawing Sheets

MICROFLUIDIC MULTI-SPLITTER

STATEMENT OF RELATED APPLICATION(S)

This application claims priority to U.S. patent application Ser. No. 60/359,323, filed Feb. 23, 2002.

FIELD OF THE INVENTION

The present invention relates to the controlled splitting of fluid volumes in microfluidic conduits.

BACKGROUND OF THE INVENTION

There has been a growing interest in the application of microfluidic systems to a variety of technical areas, including such diverse fields as biochemical analysis, medical diagnostics, chemical synthesis, and environmental monitoring. For example, use of microfluidic systems for acquiring chemical and biological information presents certain advantages. In particular, microfluidic systems permit complicated processes to be carried out using very small volumes of fluid. In addition to minimizing sample volume, microfluidic systems increase the response time of reactions and reduce reagent consumption. Furthermore, when conducted in microfluidic volumes, a large number of complicated biochemical reactions and/or processes may be carried out in a small area, such as in a single integrated device. Examples of desirable applications for microfluidic technology include analytical chemistry; chemical and biological synthesis, DNA amplification; and screening of chemical and biological agents for activity, among others.

Traditional methods for constructing microfluidic devices have used surface micromachining techniques borrowed from the silicon fabrication industry. According to these techniques, microfluidic devices have been constructed in a planar fashion, typically covered with a glass or other cover material to enclose fluid channels. Representative devices are described, for example, in some early work by Manz, et al. (Trends in Anal. Chem. (1990) 10(5): 144–149; Advances in Chromatography (1993) 33: 1–66). These publications describe microfluidic devices constructed using photolithography to pattern channels on silicon or glass substrates, followed by application of surface etching techniques to remove material from a substrate to form channels. Thereafter, a cover plate is typically to the top of an etched substrate to enclose the channels and contain a flowing fluid.

More recently, a number of methods have been developed that allow microfluidic devices to be constructed from plastic, silicone or other polymeric materials. Fabrication methods include micromolding of plastics or silicone using surface-etched silicon as the mold material (see, e.g., Duffy et al., Anal. Chem. (1998) 70: 4974–4984; McCormick et al., Anal. Chem. (1997) 69: 2626–2630); injection-molding; and micromolding using a LIGA technique (see, e.g., Schomburg et al., Journal of Micromechanical Microengineering (1994) 4: 186–191), as developed at the Karolsruhe Nuclear Research Center in Germany and commercialized by MicroParts (Dortmund, Germany). LIGA and hot-embossing techniques have also been demonstrated by Jenoptik (Jena, Germany). Imprinting methods in polymethylmethacrylate (PMMA) have also been described (see, e.g., Martynova et al., Anal. Chem. (1997) 69: 4783–4789). These various techniques are typically used to fashion planar (i.e., two dimensional, or 2-D) structures that require some sort of cover to enclose microfluidic channels. Additionally, these techniques do not lend themselves to rapid prototyping and manufacturing flexibility. Moreover, the tool-up costs for such techniques are often quite high and can be cost-prohibitive A more recent method for constructing microfluidic devices uses a KrF laser to perform bulk laser ablation in fluorocarbons that have been compounded with carbon black to cause the fluorocarbon to be absorptive of the KrF laser (see, e.g., McNeely et al., "Hydrophobic Microfluidics," SPIE Microfluidic Devices & Systems IV, Vol. 3877 (1999)). This method is reported to reduce prototyping time; however, the addition of carbon black renders the material optically impure and presents potential chemical compatibility issues. Additionally, the reference is directed only to planar structures.

When working with fluids in conventional macroscopic volumes, splitting a fluid stream into two or more portions or substreams is a relatively straightforward task. Generally, bulk fluid interactions have a greater effect on fluid flow behavior than interactions between the fluid and confining surfaces. It is relatively simple to construct fluid splitting systems that will fill in a predictable manner.

Figure 1:
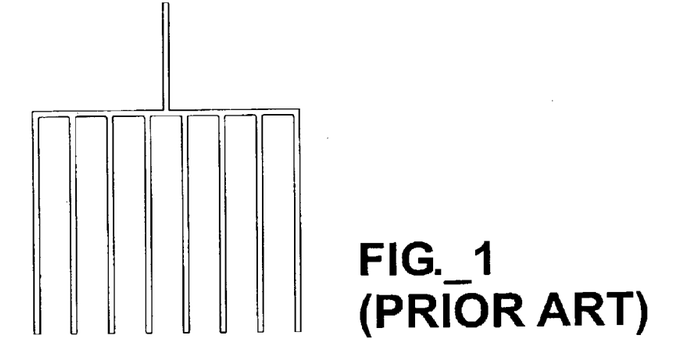
FIG. 1 is a top view of a prior art fluid splitting apparatus having a distribution manifold for supplying fluid to multiple outlet channels.

In microfluidic systems, however, achieving consistent and predictable splitting is not a trivial matter. Microfluidic systems are characterized by extremely high surface-to-volume ratios, causing surface interactions to have a much more significant effect on fluid movement. In simple terms, if a fluid stream is provided to a junction or manifold region having multiple outlet channels (such as the manifolded prior art splitting design illustrated in FIG. 1), it is difficult to predict which one or more of the outlet channels will be filled. For example, if an advancing fluid front in a microfluidic system encounters a forked region and flow is established in one branch of the fork, there is little impetus for flow to be initiated in the other branch.

It is desirable to produce relatively compact microfluidic systems to promote easy interface with standard laboratory instruments including detection instruments such as plate readers and dispensing equipment including automated pipettors. It is also desirable to provide microfluidic devices capable of multiple simultaneous operations with a minimal number of fluidic interfaces. As a result, it would be desirable to provide splitting utility on a microfluidic device in as compact an area as possible.

Figure 2:
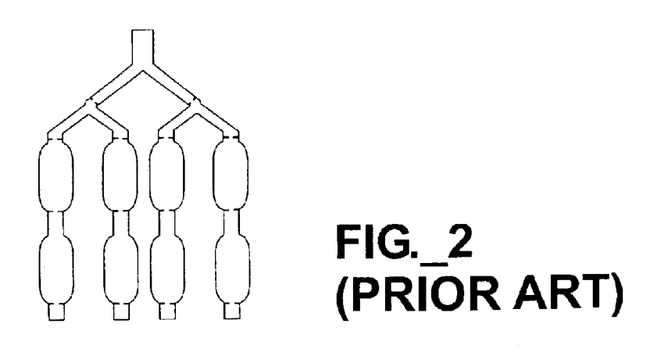
FIG. 2 is a top view of a prior art fluid splitting apparatus with multiple forked channels defined in a single layer, the apparatus having multiple short channel restrictions.

A method for controlling fluid splitting in microfluidic channels has been proposed in U.S. Pat. No. 6,296,020 ("the '020 reference"), issued on Oct. 2, 2001 to assignee BioMicro Systems, Inc. A splitting channel network including a series of "daughter" channels is defined in a single layer using micromachining techniques, with short channel narrowings or restrictions disposed at the far end of each channel to provide a pressure barrier. A splitting channel network according to the design of the '020 reference is illustrated in FIG. 2. Each generation of channel restrictions needs to provide a greater pressure barrier than the previous generation in order to promote predictable splitting. Devices according to the '020 reference, however, suffer from defects that limit their utility. To begin with, it is difficult and time-consuming to fabricate microfluidic devices with even the simplest micromachining techniques. Predictable splitting systems confined to a single device layer inherently consume a relatively large footprint on a microfluidic device, particularly when it is desirable to split to a large number of outlet channels. Additionally, the progressively increasing pressure barriers proposed in the '020 reference impose a practical limit to the number of splits that can be achieved. Notably, the '020 reference discloses no more than 4-way splitting.

In certain applications, precise and uniform splitting would be highly desirable. For example, highly parallel chemical and biological separation techniques such as liquid chromatography have been proposed, to achieve multiple separations simultaneously. Chromatography is a physical method of separation wherein components partition between two phases: a stationary phase and a mobile phase. Sample components are carried by a mobile phase through a bed of stationary phase.

In liquid chromatography applications, it is often desirable to alter the makeup of the mobile phase during a particular separation, such as by mixing two or more mobile phase components in different proportions. If multiple separation columns are provided in a single integrated (highly parallel) device and the makeup of the mobile phase is subject to change over time, then at a common linear distance from the mobile phase inlet it is desirable for mobile phase to have a substantially identical composition from one column to the next.

In light of the foregoing, there exists a need for a microfluidic splitter that is compact, easy to fabricate, and is scalable to provide uniform splitting to a large number of outlet channels.

BRIEF DESCRIPTION OF THE DRAWINGS

FIG. 4A is an exploded perspective view of a six-layer microfluidic device having a three-dimensional splitting channel network for distributing fluids to twenty-four channels or columns.

DETAILED DESCRIPTION OF PREFERRED EMBODIMENTS OF THE INVENTION

Definitions

The term "column" as used herein refers to a region of a fluidic device containing stationary phase material, typically including packed particulate matter.

The term "microfluidic" as used herein refers to structures or devices through which one or more fluids are capable of being passed or directed and having at least one dimension less than about 500 microns.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates or other stencils.

Fluidic Devices Generally

In an especially preferred embodiment, microfluidic devices according to the present invention are constructed using stencil layers or sheets to define channels and/or chambers. A stencil layer is preferably substantially planar and has a channel or chamber cut through the entire thickness of the layer. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely-dimensioned microstructures, the use of a laser to cut a stencil layer inherently involves the removal of some material. Further examples of methods that may be employed to form stencil layers include conventional stamping or die-cufting technologies. The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices using sandwiched stencil layers, including polymeric, metallic, and/or composite materials, to name a few.

Various means may be used to seal or bond layers of a device together. For example, adhesives may be used. In one embodiment, one or more layers of a device may be fabricated from single- or double-sided adhesive tape, although other methods of adhering stencil layers may be used. A portion of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. For example, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

First Preferred Fluidic Device

Figure 3A:
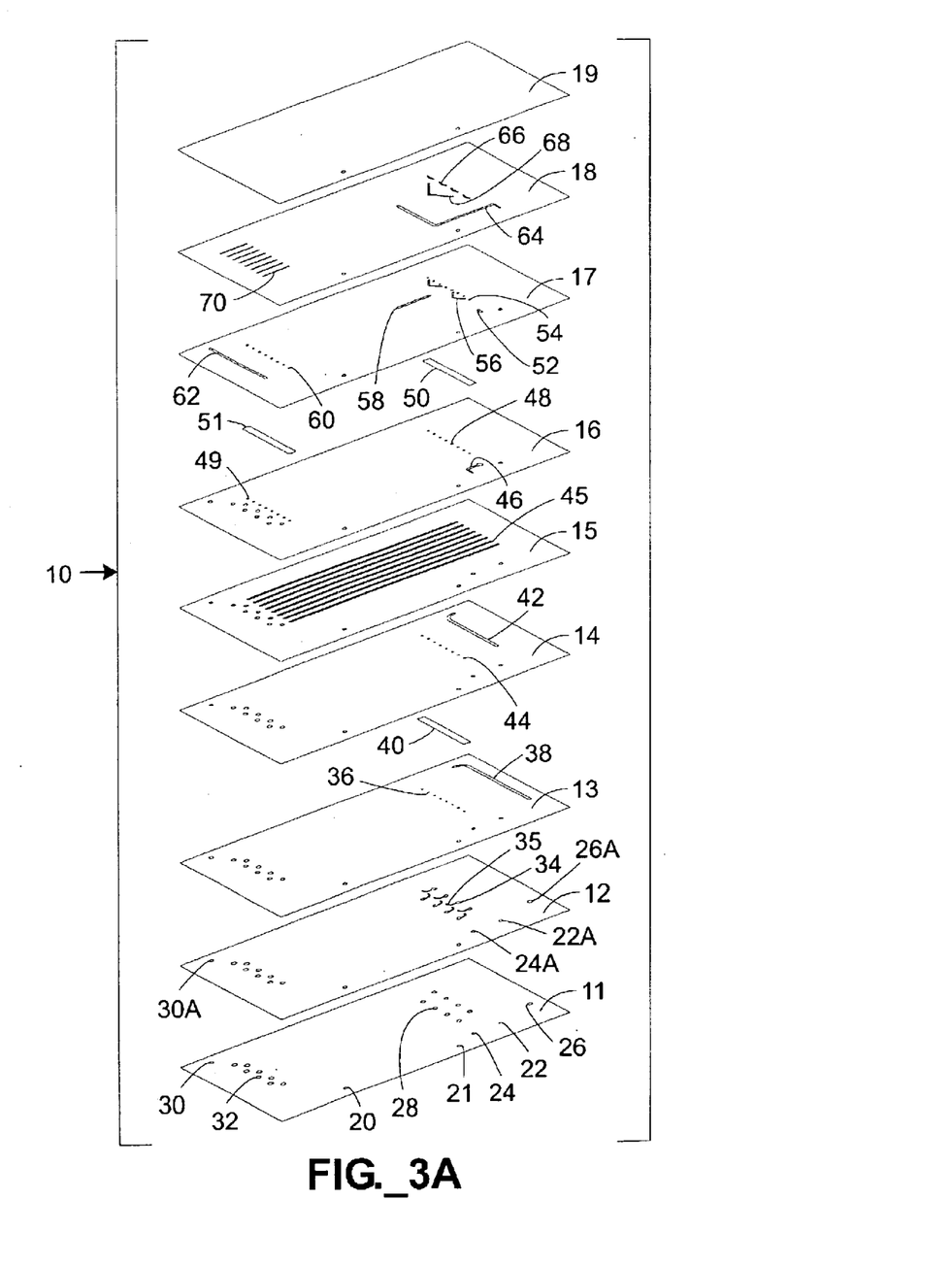
FIG. 3A is an exploded perspective view of a nine-layer microfluidic separation device having a three-dimensional splitting channel network for distributing fluids to eight separation columns.
Figure 3B:
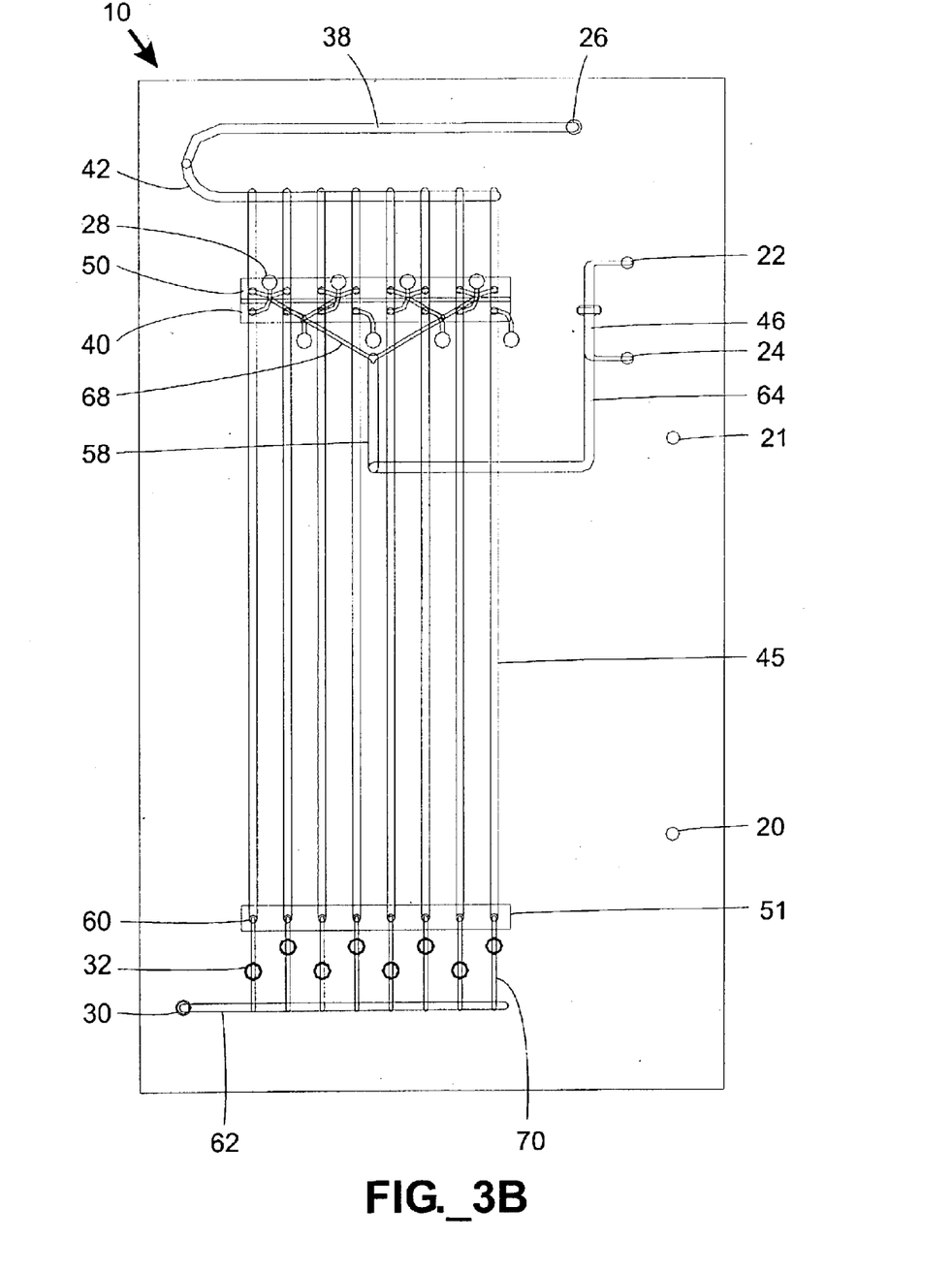
FIG. 3B is a top view of the assembled device of FIG. 3A.

In a first preferred device, a multi-layer splitting channel network supplies multiple fluid sub-streams to multiple packed column-containing channels in an integrated microfluidic separation device. For example, FIGS. 3A–3B illustrate a microfluidic separation device 10 constructed with nine layers 11–19, including multiple stencil layers 12–18. Each of the nine layers 11–19 defines two alignment holes 20, 21, which are used in conjunction with external pins (not shown) to aid in aligning the layers during construction or in aligning the device 10 with an external interface during a packing process. The first layer 11 defines several fluidic ports: two inlet ports 22, 24 are used to admit (mobile phase) solvent to the device 10; eight sample ports 28 permit sample to be introduced to eight columns (provided in channels 45); a slurry inlet port 26 is used during a column packing procedure to admit slurry to the device 10; and a fluidic port 30 that is used both (1) during the packing process to exhaust (slurry) solvent from the device 10; and (2) during operation of the separation device 10 to exit mobile phase solvent and sample from the device 10 following separation. The first through sixth layers 11–16 each define eight optical detection windows 32. Defining these windows 32 through these layers 11–16 facilitates optical detection since it reduces the amount of material between an optical detector (not shown) such as a conventional UV-VIS detector, and the samples contained in channel segments 70 downstream of the column-containing channels 45.

The second through seventh layers 12–17 define solvent vias 22A to transport a first mobile phase channel 64 defined in the eighth layer 18, with further solvent vias 24A defined in the second through fifth layers 12–15 to transport a second mobile phase solvent to the channel 46 defined in the sixth layer 16. Further vias 30A are defined in the second through sixth layers 12–16 to provide a fluid path between the fluidic port 30 and the channel 62 defined in the seventh layer 17. A via 26 defined in the second layer 12 communicates slurry from the slurry inlet port 26 to an elongate channel 38 defined in the third layer 13 during the slurry packing process. Preferably, particulate material deposited by the slurry packing process fills the channel 42 and at least a portion of the channel 38. The second layer 12 further defines eight sample channels 35 having enlarged regions 34 aligned with the sample inlet ports 28 defined in the first layer 11.

The third layer 13 defines an elongate channel 38 along with eight sample vias 36 aligned with the ends of the sample channels 35. The fourth channel defines eight sample vias 44 aligned with the vias 36 in the third channel 13. A (sample) frit 40 is placed between the third and fourth layers 13, 14. Although various frit materials may be used, the frit 40 (along with frits 50, 51) is preferably constructed from a permeable polypropylene membrane such as, for example, 1-mil thickness Celgard 2500 membrane (55% porosity, 0.209×0.054 micron pore size, Celgard Inc., Charlotte, N.C.), particularly if the layers 11–19 of the device 10 are bonded together using an adhesiveless thermal bonding method utilizing platens, such as described above. Favorable results have been obtained using this specific frit material, without noticeable wicking or lateral flow within the frit despite using a single strip of the frit membrane to serve multiple adjacent column-containing channels. As a less-preferred alternative to the single frit 40, multiple discrete frits (not shown) of various porous material types and thicknesses may be substituted. The fourth layer 14 further defines a manifold channel 42 that provides fluid communication with the separation channels 45 defined in the fifth layer 15 and the elongate channel 38 defined in the third layer 13. The separation channel 45 are preferably about 40 mils (1 mm) wide or smaller.

The sixth layer 46 defines a channel 46 that receives a second mobile phase solvent for transport to the slit 52 defined in the seventh layer 17, which facilitates mixing of the two solvents in the channel 64 downstream of the slit 52. Further defined in the sixth layer 16 are a first set of eight vias 48 for admitting mixed mobile phase solvent to the upstream end of the channels 45 and the separation columns contained therein, and a second set of eight vias 49 at the downstream end of the same channels 45 for receiving mobile phase solvent and sample. Two frits 50, 51 are placed between the sixth and the seventh layers 16, 17. The first (mobile phase solvent) frit 50 is placed immediately above the first set of eight vias 48, while the second (mobile phase+sample) frit 51 is placed immediately above the second set of eight vias 49 and below a similar set of eight vias 60 defined in the seventh layer 17.

A splitting channel network for splitting a single inlet stream to eight outlet substreams is defined in the seventh and eighth layers 17, 18. The seventh layer 17 defines an inlet channel segment 58, two medium forked channel segments 56, and eight vias 54 for communicating mobile phase solvent through the frit 50 and the vias 48 to the separation columns contained in the channels 45 defined in the fifth layer 15. The eighth layer 18 defines a large forked channel 68 and four small forked channels 66. Each of the forked channels comprises two diverging (branch) channel segments joined at an apex. Several overlap regions are present to permit fluid to flow between the various channels of the splitting network. For example, the inlet channel 58 and the apex of the large forked channel 68 meet at one overlap region; the distal ends of the large forked channel 68 and the apexes of the medium forked channels 56 meet at two more overlap regions; and the distal ends of the medium forked channels 56 and the apexes of the small forked channels 66 meet at four more overlap regions.

The overlap regions aid in promoting even splitting. As fluid enters each forked channel, the fluid may initially travel down only one of the two branch segments. However, when the fluid front reaches the end of one branch segment, it momentarily pauses at the overlap region, ostensibly due to a slight impedance to fluid flow, and fluid fills the second branch before fluid in either segment proceeds through the overlap associated with either channel end. This reduces the likelihood that fluid will travel through the network in a single path without splitting into sub-streams.

Another factor that promotes even splitting in the device 10 is the presence of large impedance regions (namely, column-containing channels 45) downstream of each separate outlet from the network. This helps ensure that the entire network (i.e. forked channels 68, 56, 66) is filled before any substream proceeds into the column-containing channels 45.

Another desirable characteristic is that each fluid path through the splitting network is characterized by substantially the same volume (e.g., the same length for channels having identical cross-sections). In liquid chromatography applications, it is often desirable to alter the makeup of the mobile phase during a particular separation. The device 10 contains multiple separation columns 45. Because the mobile phase composition supplied to the separation device 10 is subject to change with time, equal volume fluid paths through the splitter help ensure substantially identical mobile phase composition from one column to the next at a common linear distance from the mobile phase inlet.

The seventh layer 17 further defines a transverse manifold channel 62 that receives mobile phase solvent and sample during separation, and that receives (slurry) solvent during column packing, for routing such fluids through vias 30A to the fluidic exit port 30. The eighth layer 18 defines eight parallel channel segments 70 downstream of the frit 51 for receiving (mobile phase) solvent and sample (during separation) or (slurry) solvent (during slurry packing), and for transporting such fluid(s) to the manifold channel 62 defined in the seventh layer 17. The ninth layer 19 serves as a cover for the channel structures defined in the eighth layer 18.

Figure 3C:
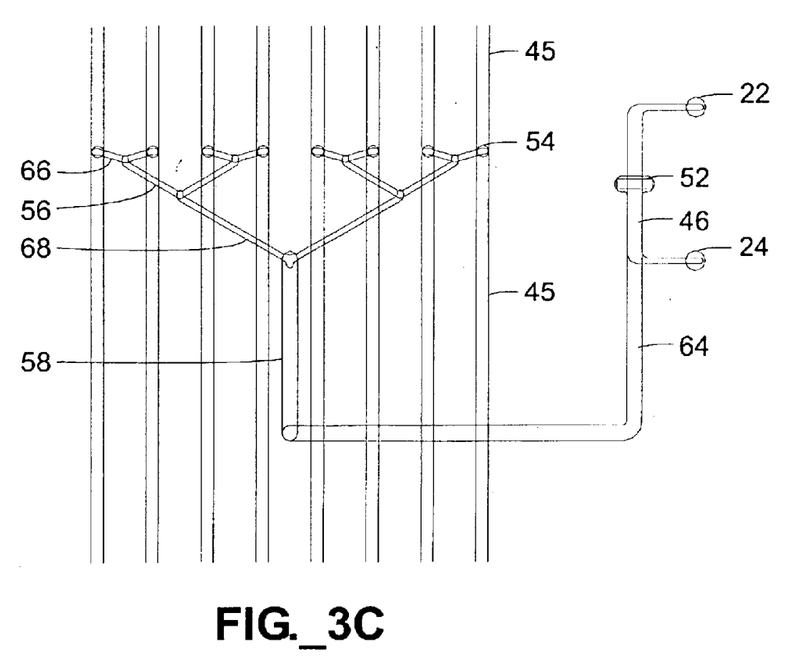
FIG. 3C is an enlarged top view of a portion of the device of FIGS. 3A–3B showing solvent inlet ports, a mixing region, and a splitting network for splitting and distributing a solvent mixture among eight columns.

FIG. 3B is a top view of the assembled device 10 of FIG. 3A. FIG. 3C provides an expanded view of a portion of the device 10 showing the mixing and splitting channel structures that communicate mobile phase solvent to the column-containing channels 45. During operation of the device 10, a first mobile phase solvent is injected into a first solvent inlet port 22 and flows into channel 64. A second mobile phase solvent is injected into a second solvent inlet port 24 and flows through the channel segment 46 through a slit 52 where it is layered with and joins the first solvent in the channel 64. The two layered solvents mix in the channel 64 and subsequent channel segment 58, whereafter the mixed solvent stream is split into eight portions or substreams as it travels through the forked channels 68, 56, 66. The eight solvent mixture substreams are then injected through vias 54 and 48 into the (column-containing) separation channel 45. For simplicity, the frit 50 disposed between the vias 54 and 48 have been omitted in FIG. 3C, although this frit 50 is properly included in FIGS. 3A–3B.

Preferably, the various layers 11–19 of the device 10 are fabricated from un-oriented polypropylene and bonded using an adhesiveless thermal bonding method utilizing platens, as described above. This construction method yields chemically-resistant devices having high bond strength, both desirable attributes for withstanding a column packing process and subsequent operation to provide separation utility.

While the device 10 illustrated in FIGS. 3A–3C represents a preferred fluidic separation device, a wide variety of other fluidic devices utilizing splitting channel networks may be constructed. In certain embodiments, fluidic device may include one or more tubes, particularly capillary tubes. For example, capillary tubes may be embedded in one or more channels of a microfluidic device.

Second Preferred Fluidic Device

Figure 4B:
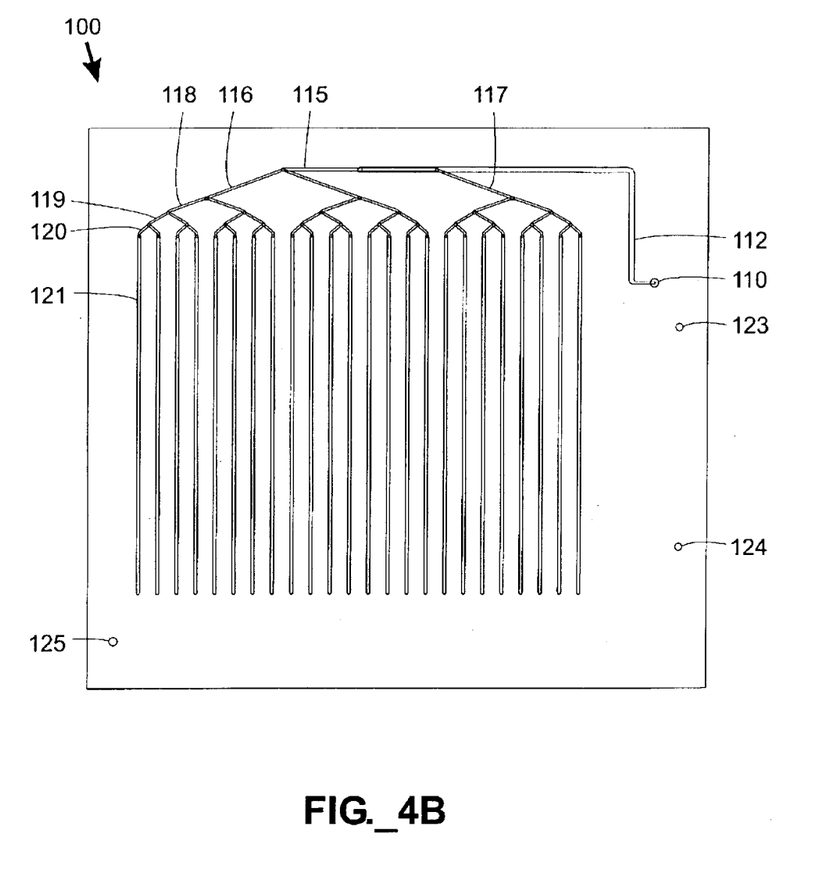
FIG. 4B is a top view of the assembled device of FIG. 4A.

Compact splitting networks having more than eight outlets can be constructed. For example, a second preferred fluidic device 100 containing a 24-outlet splitting network is shown in FIGS. 4A–4B. The device 100 may be constructed in a similar manner to the device 10 described in connection with FIGS. 3A–3C. The device 100 is constructed in six layers 101–106, including stencil layers 102–105. Each of the six layers 101–106 define alignment holes 123–125 to assist in aligning the layers during assembly. Preferably, fixed alignment pins (not shown) conforming to the size and spacing of the alignment holes 123–125 are used to promote precise alignment between layers.

Starting from the bottom, the first layer 101 defines an inlet port 110 and twenty-four outlet ports 122. The second layer 102 defines an inlet channel 112 and twenty-four vias 122A. The third layer 103 defines a via 114 and twenty-four parallel channels 121.

A 24-way splitting channel network is defined in the fourth and fifth layers 104–105. The fourth layer 104 defines a channel segment 115, three medium forked channels 118, and twelve tiny forked channels 120. The fifth layer 105 defines a large forked channel 116, a channel segment 117, and six small forked channels 119. Each of the forked channels comprises two diverging (branch) channel segments joined at an apex. The channel segment 117 resembles one segment of the large forked channel 116.

Several overlap regions are present to permit fluid to flow between the various channels of the splitting network. For example, the inlet channel 112 and the straight channel 115 overlap through via 114; the straight channel 115 and the apex of the large forked channel 116 meet at another overlap region; the straight channel segment 115 and the channel segment 117 meet at yet another overlap region; the distal ends of the large forked channel 116 and the apexes of two medium forked channels 118 meet at two more overlap regions; the channel segment 117 and the apex of the other medium forked channel 118 meet at another overlap region; the distal ends of the medium forked channels 118 and the apexes of the small forked channels 119 meet at six more overlap regions; and the distal ends of the small forked channels 119 and the apexes of the tiny forked channels 120 meet at twelve additional overlap regions.

In operation, fluid supplied to the inlet port 110 flows through the inlet channel 112 and the via 114 into the straight channel 115. Both ends of the straight channel 115 terminates at overlap regions, thus providing two fluid paths through the channel 115. Typically, an advancing fluid front initially flows in one direction through the channel 11 5 toward a first overlap region, pauses momentarily at the overlap, and then the fluid fills the channel 115 to the other end and overlap region. Ultimately, fluid flows through both ends of the channel 115 to enter the large forked channel 116 and the channel 117. From the channels 116, 117, fluid is split into the medium forked channels 118, then split again into the small forked channels 119, and split yet again into the tiny forked channels 120 before being provided to the twenty-four parallel channels 121. Preferably, each channel 121 provides a relatively high and substantially equal impedances, which helps promote even fluid splitting between the channels 121. For example, these channels may be packed with particulate. Ultimately, the splitting network of the device 100 may be adapted to a twenty-four way microfluidic separation (e.g., liquid chromatography) device that incorporates features of the device 10 described in connection with FIGS. 3A–3C.

Figure 5:
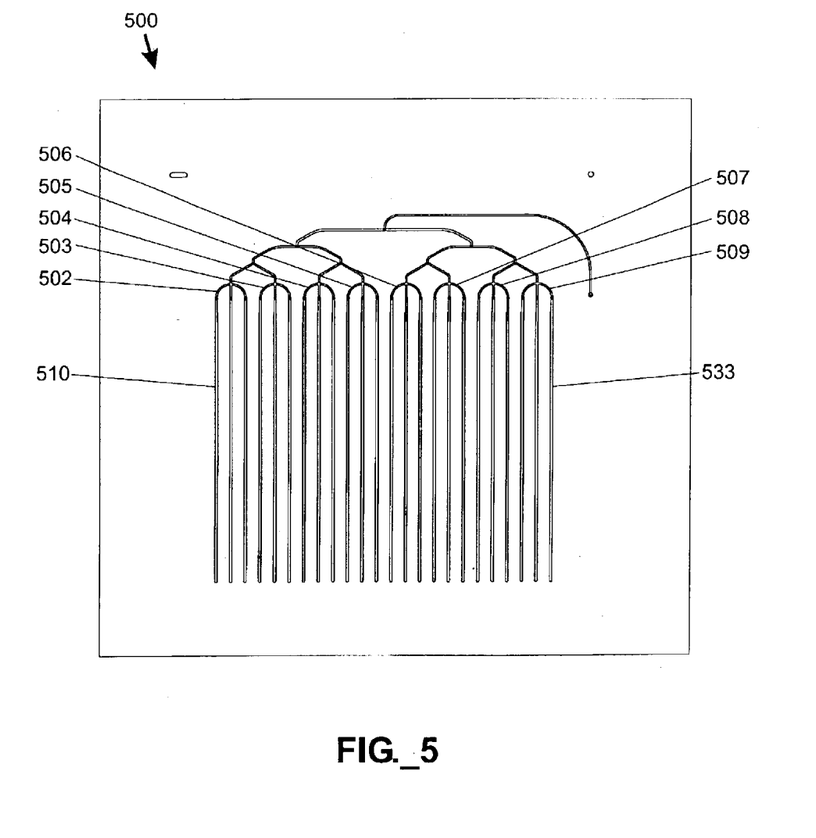
FIG. 5 is a top view of an alternate embodiment of a twenty-four channel or twenty-four column microfluidic device.

Of course, the forked channels described above may split into any suitable number of channels. For example, in an alternative embodiment, shown in FIG. 5, a twenty-four column microfluidic device 500 is provided. The device 500 may be constructed in a similar manner to the device 100 described in connection with FIGS. 4A–4B and the device 10 described in connection with FIGS. 3A–3C. The device 500 includes forked channels 502–509 that have three forks each. It should also be noted that, although the forks of the forked channels 502–509 channels are not exactly the same length, even division of flow to each of the twenty-four columns 510–533 (reference numbers 511–532 omitted for clarity) is provided because the difference in length between each fork of the forked channels 502–509 is negligible. In a similar manner, other devices (not shown) may be constructed using forked channels having any number of forks.

Third Preferred Fluidic Device

Figure 6A:
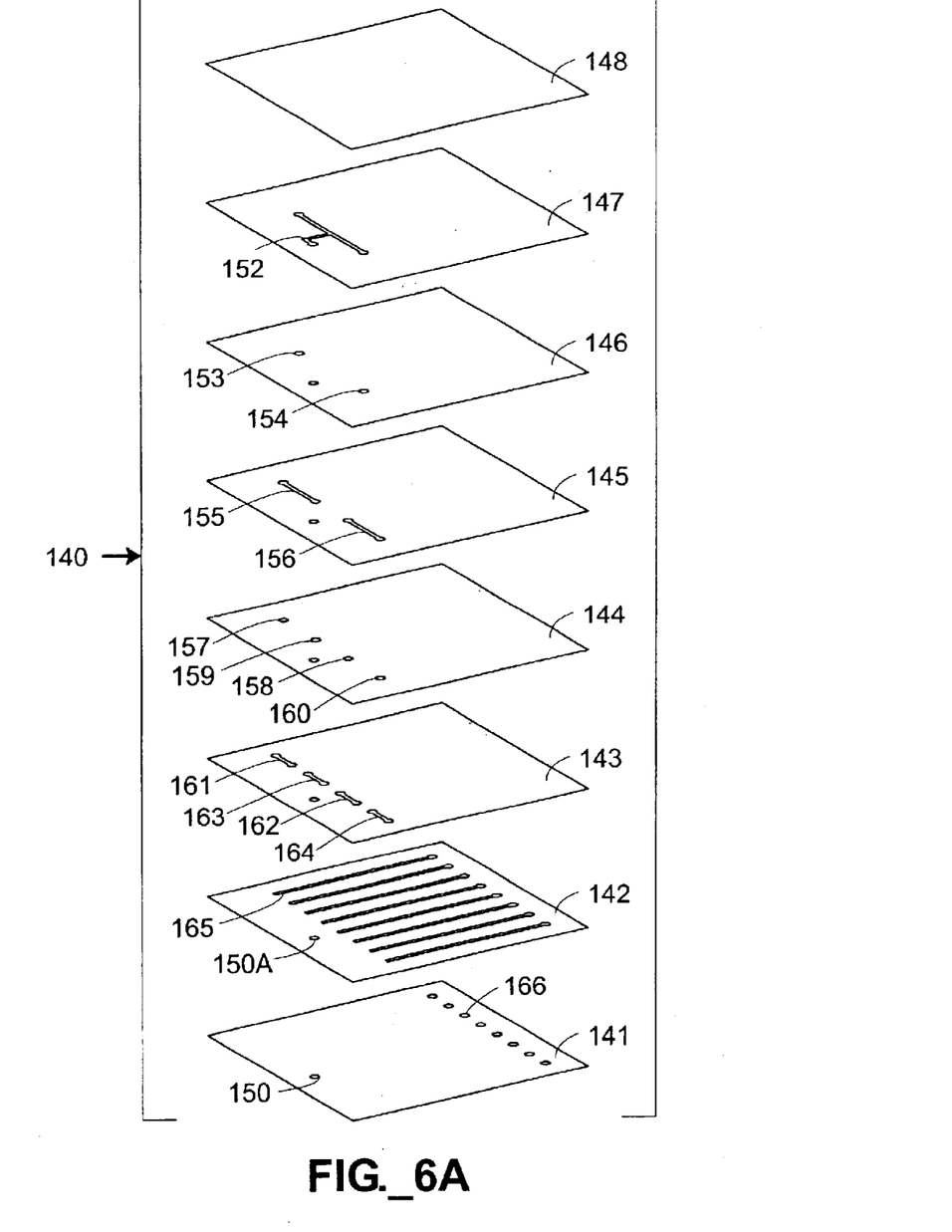
FIG. 6A is an exploded perspective view of an eight-layer microfluidic device having a first overlapping three-dimensional splitting channel network for distributing fluids to eight channels or columns.
Figure 6B:
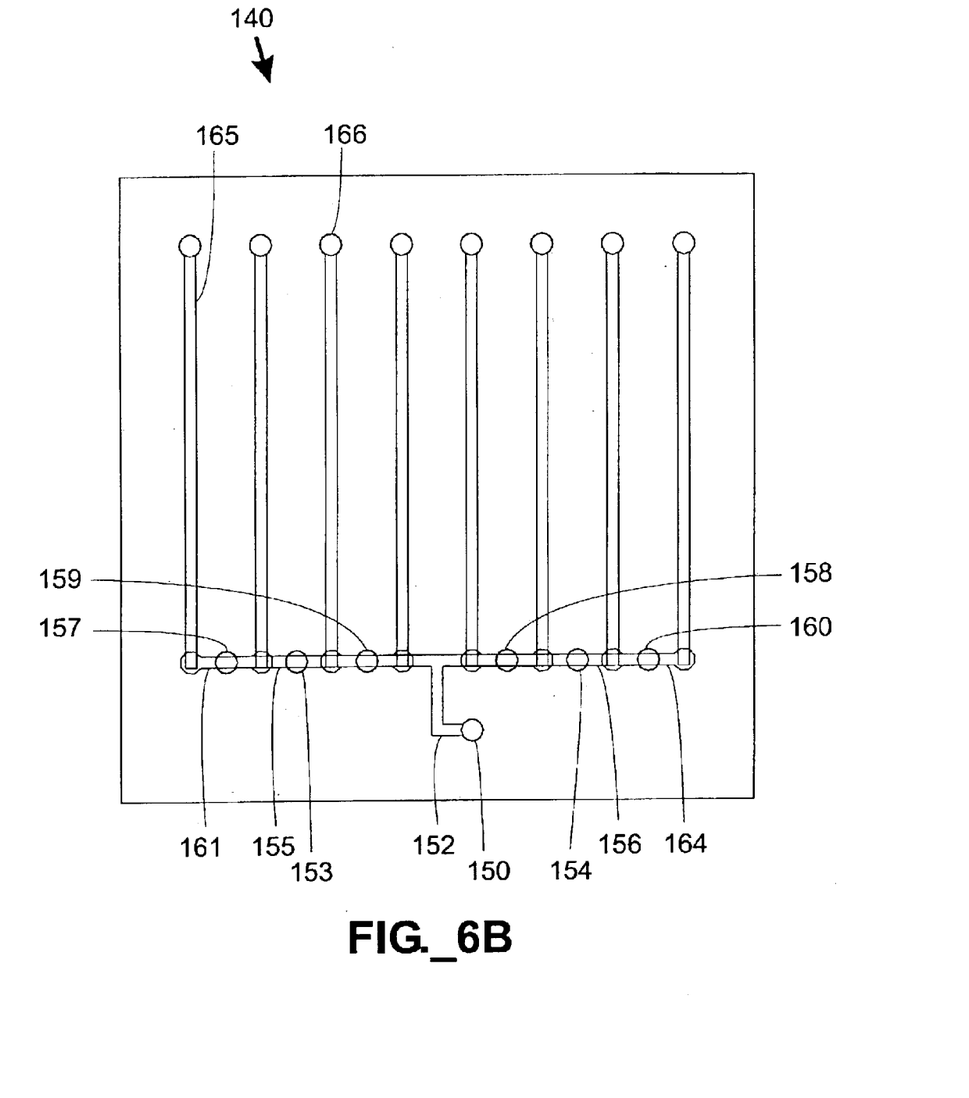
FIG. 6B is a top view of the assembled device of FIG. 6A.

Highly compact multi-splitting networks may be constructed with intermediate spacer layers. To promote extremely compact designs, forked channels may be reduced to straight channels and combined with vias in adjacent layers. For example, a third preferred fluidic device 140 containing an eight-outlet splitting network is shown in FIGS. 6A–6B. The device 140 is constructed in eight layers 141–148, including stencil layers 142, 143, 145, 147.

The first layer 141 defines a fluidic inlet port 150 and eight fluidic outlet ports 166. The second through sixth layers 142–146 define a via 150A. The second layer 142 further defines eight outlet channels 165. The third layer 143 defines four third-generation splitting channels 161–164. The fourth layer 144 defines four vias 157–160. The fifth layer 145 defines two second-generation splitting channels 155–156. The sixth layer 146 defines two vias 153, 154. The seventh layer 157 defines a first-generation T-shaped splitting channel 152. The eighth layer 148 serves as a cover to enclose the channel 152 defined in the adjacent seventh layer 157. Several overlap regions are present to permit fluid to flow between the various channels of the splitting network. For example, certain overlap regions correspond to and include the vias 153, 154, and 157–160. Additional overlaps are present between the third-generation splitting channels 161–164 and the outlet channels 165.

In operation, fluid supplied to the inlet port 150 flows through the vias 150A and into the first-generation ("gen-1") splitting channel 152, which has two outlets disposed above vias 153, 154. Fluid splits into two substreams through the gen-1 channel 152, and these substreams flow through the vias 153, 154 into the two gen-2 splitting channels 155, 156. From the gen-2 splitting channels 155–156, four substreams are formed and flow through the vias 157–160 into the four gen-3 splitting channels 161–164. Eight substreams emerge from the four gen-3 splitting channels 161–164 and flow into the eight parallel channels 165.

Fourth Preferred Fluidic Device

Figure 7A:
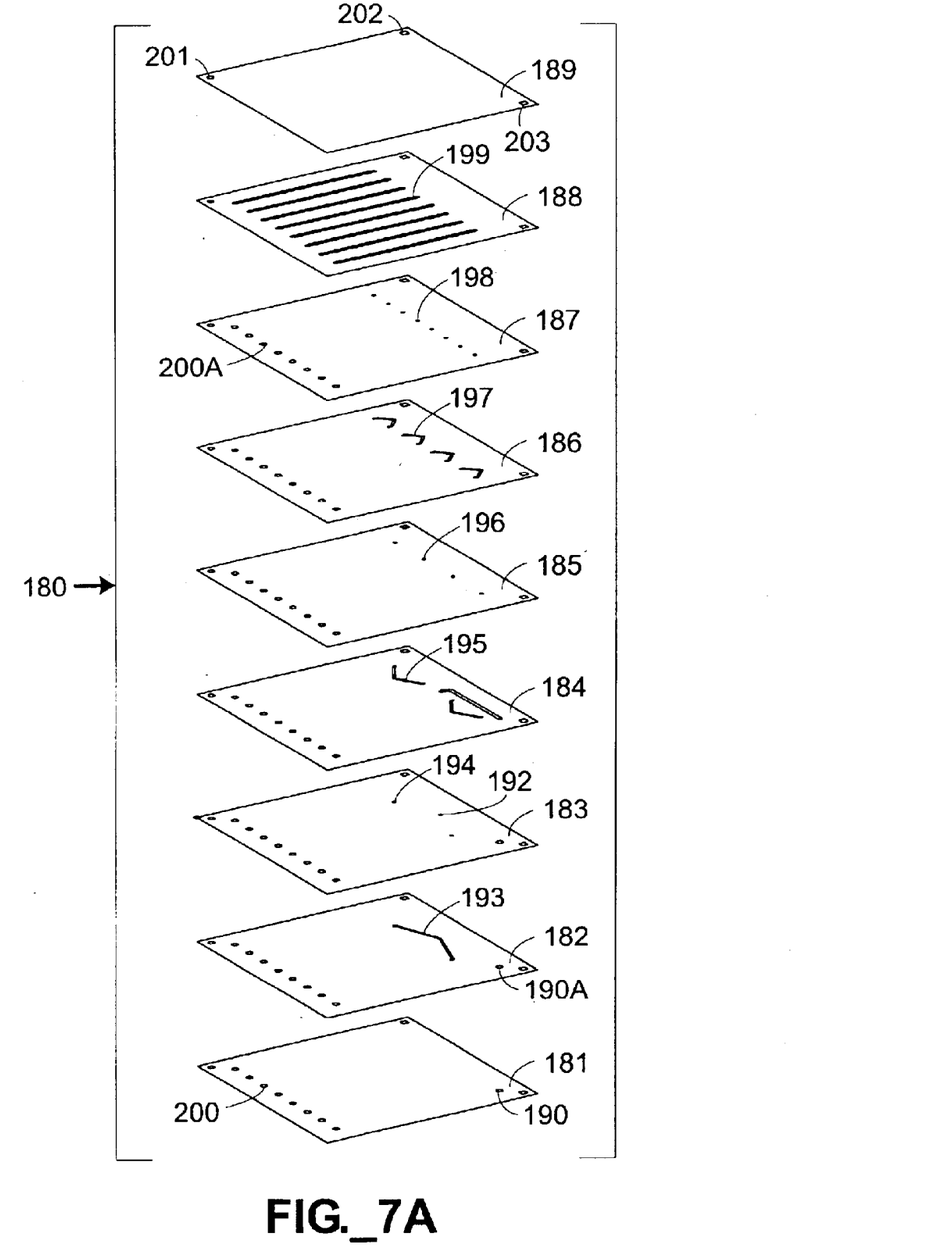
FIG. 7A is an exploded perspective view of a six-layer microfluidic device having a second overlapping three-dimensional splitting channel network for distributing fluids to eight channels or columns.
Figure 7B:
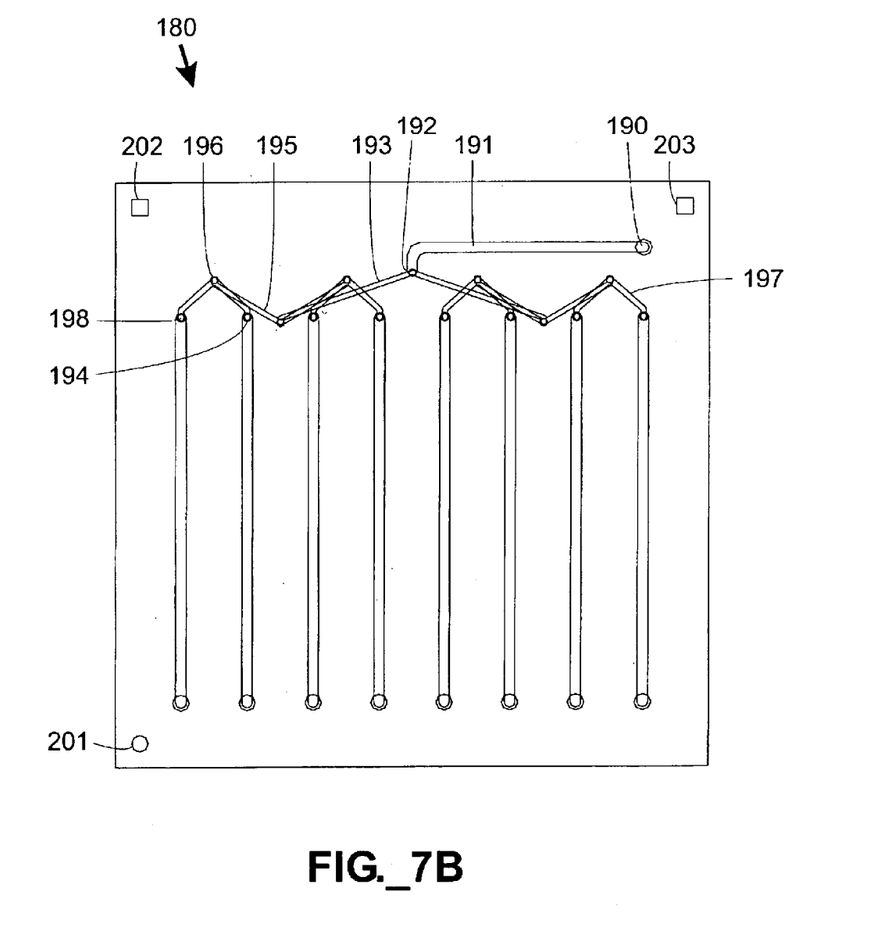
FIG. 7B is a top view of the assembled device of FIG. 7A.

A further embodiment is shown in FIGS. 7A–7B, which illustrates a fourth preferred fluidic device 180 containing an eight-outlet splitting network. The device 180 is constructed in nine layers 181–189, including four stencil layers 182, 184, 186, 188. Each of the nine layers 181–186 define alignment holes 201–203 to assist in aligning the layers during assembly.

Starting from the bottom, the first layer 181 defines one fluidic inlet port 190 and eight fluidic outlet ports 200. The second and third layers 182, 183 define a via 190A. The second through seventh layers 182–187 each define eight vias 200A. The second layer 182 further defines a large forked channel 191. The third layer defines a via 192 and two vias 193. The fourth layer 184 defines an inlet channel 194 and two medium forked channels 195. The fifth layer 185 defines four vias 196. The sixth layer 186 defines four small forked channels 197. The seventh layer 187 defines eight vias 198. The eighth layer 188 defines nine parallel channels 199. The ninth layer 189 serves as a cover to enclose the channels 199 defined in the eighth layer 188. Several overlap regions are present to permit fluid to flow between the various channels of the splitting network. For example, overlap regions correspond to and include the vias 193, 196, 198.

In operation, fluid supplied to the inlet port 190 flows through the vias 190A, the inlet channel 194, and the via 192 into the large forked channel 191. The fluid splits into two substreams in the large forked channel 191, and these substreams are supplied to the medium forked channels 195 through the vias 193. The fluid splits into four substreams in the medium forked channels 195, and these four substreams are supplied through the vias 196 to the small forked channels 197. From the small forked channels 197, eight fluid substreams flow through the vias 198 into the eight parallel channels 199. These substreams may exit the device through the vias 200A and outlet ports 200. Notably, as shown in FIG. 7B, from a top view the direction of bulk fluid flow appears to reverse within the device 180.

Fifth Preferred Fluidic Device

Figure 8A:
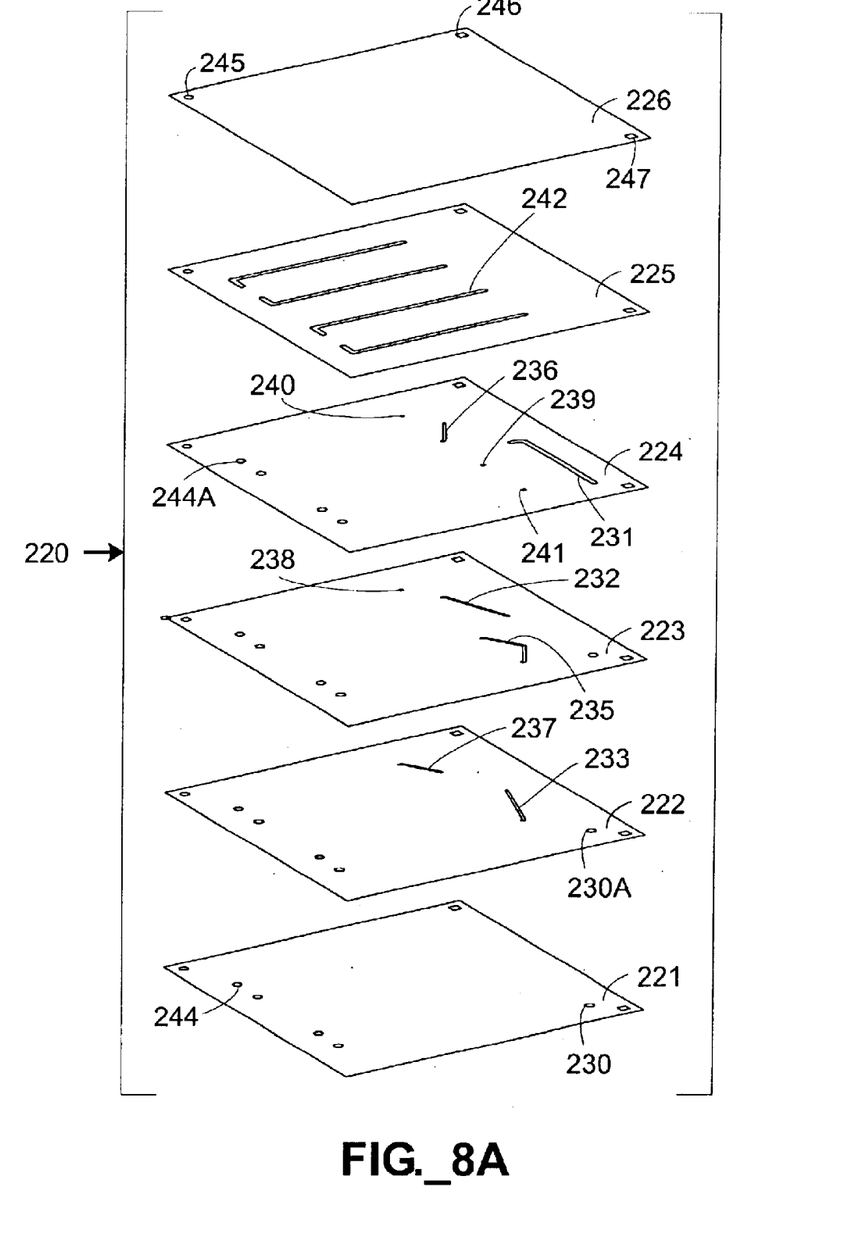
FIG. 8A is an exploded perspective view of a six-layer microfluidic device having an alternative three-dimensional splitting channel network for distributing fluids to eight channels or columns.
Figure 8B:
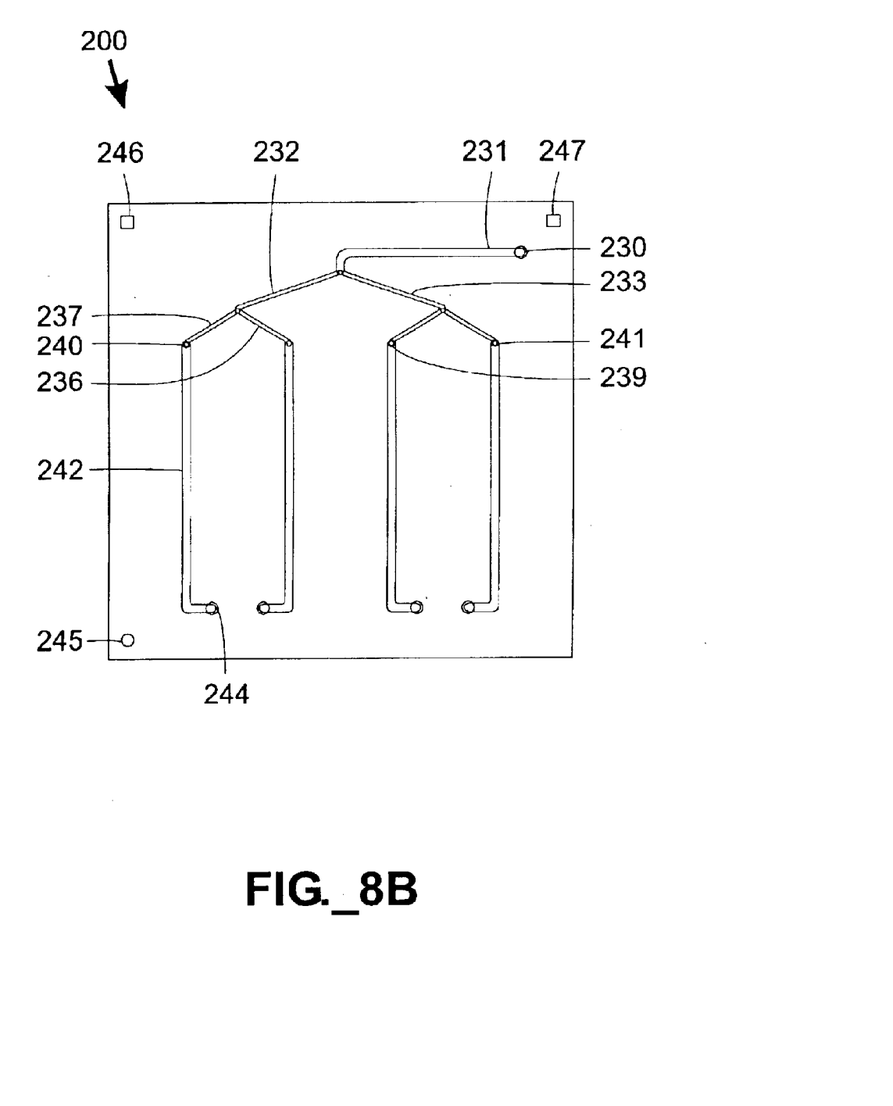
FIG. 8B is a top view of the assembled device of FIG. 8A.

In another embodiment, 'composite' forked channels consisting of segments defined in different layers may be used in a microfluidic splitting network. Such an embodiment provides enhanced design flexibility, particularly for complicated devices having a high density of features. One example of a preferred fluidic device 220 containing a four-outlet splitting network with composite forked channels is shown in FIGS. 8A–8B. The device 220 is constructed in six layers 221–226, including stencil layers 222–225. Each of the six layers 221–226 define alignment holes 245–247 to assist in aligning the layers during assembly.

Starting from the bottom, the first layer 221 defines an inlet port 230 and four outlet ports 244. The second and third layers 222, 223 define a via 230A, and the second through fourth layers 222–224 each define four vias 244A. The second layer 222 further defines a large channel segments 233 and a small channel segment 237. The third layer 223 defines a large channel segment 232, a small forked channel 235, and a via 238. The fourth layer 224 defines an inlet channel 231, a small channel segment 236, and vias 239–241. The fifth layer 225 defines four outlet channels 242. The sixth layer 226 serves as a cover to enclose the channels 244 defined in the fifth layer 225.

The large channel segments 232, 233 function in concert like a large forked channel. Similarly, the small channel segments 236, 237 function together like a small forked channel.

The device 220 includes several overlap regions. The inlet channel 231 overlaps both large channel segments 232, 233 at a first overlap region. The distal end of the large channel segment 232 overlaps small channel segments 236, 237 at another overlap region. The distal end of the large channel segment 233 overlaps the apex of the small forked channel segment 235. Overlaps involving the outlet channels 242 are also present with the small forked channel through vias 239, 241; with the small channel segment 236; and with the small channel segment 237 through vias 238, 240.

In operation, fluid supplied to the inlet port 230 flows through the vias 230A into the inlet channel 231. The fluid is split into two substreams in large channel segments 232, 233. Thereafter, the two substreams are split into four substreams through the small channels 236, 237 and the small forked channel 235. These four substreams are provided to the channels 242, and may exit the device 220 through vias 244A and the outlet ports 244.

The particular devices and construction methods illustrated and described herein are provided by way of example only, and are not intended to limit the scope of the invention. The scope of the invention should be restricted only in accordance with the appended claims and their equivalents.

What is claimed is:

1. A microfluidic device comprising:
   a plurality of device layers
   wherein at least two of the device layers are stencil layers;
   wherein the stencil layers define a first forked channel, a second forked channel, and a third forked channel;
   wherein the second forked channel is in fluid communication with the first forked channel at a first overlap region;
   wherein the third forked channel is in fluid communication with the first forked channel at a second overlap region.

2. The microfluidic device of claim 1 wherein the second forked channel and the third forked channel are defined in different stencil layers.

3. The microfluidic device of claim 1 wherein the first forked channel, second forked channel, and third forked channel define a plurality of fluid flow paths, each fluid flow path having substantially the same length.

4. The microfluidic device of claim 3 wherein portions of at least two of the fluid flow paths of the plurality of fluid flow paths are overlapping.

5. The microfluidic device of claim 1 wherein the first forked channel, second forked channel, and third forked channel define a plurality of fluid flow paths, each fluid flow path having substantially the same volume.

6. The microfluidic device of claim 5 wherein portions of at least two of the fluid flow paths of the plurality of fluid flow paths are overlapping.

7. The microfluidic device of claim 1 wherein any of the forked channels are straight.

8. The microfluidic device of claim 1 wherein any of the forked channels has more than two forks.

9. The microfluidic device of claim 1 wherein the stencil layers include a polymeric material.

10. The microfluidic device of claim 9 wherein the polymeric material is a polyolefin.

11. The microfluidic device of claim 10 wherein the polyolefin is polypropylene.

12. The microfluidic device of claim 1 wherein the device layers are adhesivelessly bonded.

13. A microfluidic splitting device comprising:
   a first stencil layer defining a first forked channel; and
   a second stencil layer defining a second forked channel and a third forked channel;
   wherein the first forked channel is in fluid communication with the second forked channel at a first overlap region;
   wherein the first forked channel is in fluid communication with the third forked channel at a second overlap region.

14. The microfluidic splitting device of claim 13 wherein the first stencil layer and the second stencil layer are adjacent.

15. The microfluidic splitting device of claim 13, further comprising a spacer layer disposed between the first stencil layer and the second stencil layer, the spacer layer defining a first aperture along the first overlap region and defining a second aperture along the second overlap region.

16. The microfluidic device of claim 13 wherein the first forked channel, second forked channel, and third forked channel define a plurality of fluid flow paths, each fluid flow path having substantially the same length.

17. The microfluidic device of claim 16 wherein portions of at least two of the fluid flow paths of the plurality of fluid flow paths are overlapping.

18. The microfluidic device of claim 13 wherein the first forked channel, second forked channel, and third forked channel define a plurality of fluid flow paths, each fluid flow path having substantially the same volume.

19. The microfluidic device of claim 18 wherein portions of at least two of the fluid flow paths of the plurality of fluid flow paths are overlapping.

20. The microfluidic device of claim 13 wherein any of the forked channels are straight.

21. The microfluidic device of claim 13 wherein any of the forked channels has more than two forks.

22. The microfluidic device of claim 13 wherein the stencil layers include a polymeric material.

23. The microfluidic device of claim 22 wherein the polymeric material is a polyolefin.

24. The microfluidic device of claim 23 wherein the polyolefin is polypropylene.

* * * * *